United States Patent
Snelling et al.

[11] Patent Number: 6,154,277
[45] Date of Patent: Nov. 28, 2000

[54] ABSOLUTE INTENSITY MEASUREMENTS IN LASER INDUCED INCANDESCENCE

[75] Inventors: David R. Snelling, Almonte; Gregory J. Smallwood, Orleans; Ömer L. Gülder, Ottawa, all of Canada

[73] Assignee: National Research Council of Canada, Ottawa, Canada

[21] Appl. No.: 09/315,155

[22] Filed: May 20, 1999

Related U.S. Application Data

[60] Provisional application No. 60/086,506, May 22, 1998.

[51] Int. Cl.$^7$ ..................................................... G01N 21/00
[52] U.S. Cl. ........................... 356/338; 356/336; 250/575
[58] Field of Search ..................................... 356/336, 338, 356/339, 342, 347, 348, 43, 46, 47, 315; 250/575, 574, 554; 372/69

[56] References Cited

U.S. PATENT DOCUMENTS

| | | | |
|---|---|---|---|
| 3,392,625 | 7/1968 | Land ......................................... | 356/46 |
| 5,180,921 | 1/1993 | Moreau et al. ......................... | 250/554 |
| 5,285,467 | 2/1994 | Scheps ..................................... | 372/69 |
| 5,920,388 | 6/1999 | Sandberg et al. ....................... | 356/315 |

*Primary Examiner*—Hoa Q. Pham
*Assistant Examiner*—Sang H. Nguyen
*Attorney, Agent, or Firm*—Freedman & Associates

[57] ABSTRACT

The invention relates to a method and an apparatus for the determination of particle volume fractions with laser induced incandescence (LII) using absolute light intensity measurements. This requires a knowledge of the particle temperature either from a numerical model of particulate heating or experimental observation of the particulate temperature. Further, by using a known particle temperature a particle volume fraction is calculated. This avoids the need for a calibration in a source of particulates with a known particle volume fraction or particle concentration. The sensitivity of the detection system is determined by calibrating an extended source of known radiance and then this sensitivity is used to interpret measured LII signals. This results in a calibration independent method and apparatus for measuring particle volume fraction or particle concentrations. A modeling process involves a solution of the differential equations describing the heat/energy transfer of the particle and surrounding gas, including parameters to describe vaporization, heat transfer to the medium, particle heating etc. The solution gives temperature and diameter values for the particles over time. These values are then converted to radiation values using Planck's equation.

24 Claims, 8 Drawing Sheets

ABSOLUTE INTENSITY MEASUREMENTS IN LASER INDUCED INCANDESCENCE

This application claims the benefit of U.S. Provisional No. 60/086,506 filed May 22, 1998.

Field of the Invention

This invention relates to a method and an apparatus for absolute light intensity measurements in Laser Induced Incandescence (LII) and more particularly to absolute light intensity measurements in LII for a determination of a volume fraction of particulate matter.

BACKGROUND OF THE INVENTION

The presence of particulate matter, such as soot particles, in the environment has brought about an increased interest in the development of methods and devices for the determination of particulate concentration. The emission of soot from engines, power generation facilities, incinerators, or furnaces, for example, represents a loss of useful energy and further is a serious environmental pollutant and a health risk. However, the presence of soot in flames can also have positive effects. For example, the energy transfer from a combustion process is largely facilitated by the radiative heat transfer from soot. Thus, to understand soot formation and develop control strategies for soot emission or formation, measurements of soot concentrations are necessary. Laser Induced Incandescence (LII) is a good diagnostic tool for measurements of particulates as the LII signal is proportional to a particle volume fraction.

According to Planck's law all objects emit electromagnetic radiation. This radiation is invisible to the unaided eye for temperatures below 900° K. However, if an object is heated to temperatures exceeding 3000° K., the emitted light intensity of all visible wavelengths is sufficient to make the object appear white-hot, i.e. incandescence occurs. The intensity of the electromagnetic radiation increases with the temperature of the object and the peak wavelength of the emission shifts towards shorter wavelengths. In laser induced incandescence (LII) a volume of gas containing particulate matter, e.g. soot, is exposed to a pulsed high-intensity laser light source. The particulate matter or particles absorb laser light energy, heating to temperatures far above the surrounding medium. At these elevated temperatures, for example at about 4000°–4500° K. in the case of soot, the particles incandesce strongly throughout the visible and near infrared region of the light spectrum. The maximum particle temperature is controlled by the point at which particle evaporation becomes the predominant heat loss mechanism. -Any further increase in laser light energy then tends to result in an increase in the evaporation rate rather than an increase in particle temperature. In accordance with Planck's radiation law, the radiative emission at these elevated temperatures increases greatly in intensity and shifts to blue light wavelengths as compared with the non-laser heated particle and flame gases. Thus the LII incandescence signal is readily isolated from natural flame emission. Because of the rapid time scale and good spatial resolution, as well as its large dynamic range, LII is well suited as an optical diagnostic to measure particle volume fraction in turbulent, i.e. time-varying, combustion and practical devices. The technique provides high temporal and spatial resolution not provided by previous methods.

At present there is a need for real-time airborne particulate concentration measurements and for soot measurements in turbulent combustion environments. In addition spatially resolved measurements are needed.

In order to measure particulate matter in a turbulent flame the following requirements have to be met: good spatial resolution, good temporal resolution, discrimination against flame radiation, and a large dynamic range. Turbulent flames are found in most practical combustors, such as gasoline engines, Diesel engines, gas turbine engines, furnaces, and boilers, and the control of emitted particles is required to reduce health risks.

Current methods for measuring diesel particulates are the Bosch Smoke Number and the direct mass sampling. In the Bosch Smoke Number methods particulates are collected on filter paper from a portion of the exhaust stream and the light transmission through collected sample is measured. This is compared against a calibration chart to determine the particle mass flow. This method has a poor time and spatial resolution. The direct mass sampling method is the official method of the EPA and measures the mass of soot from a difference of the mass of the soot on a filter and subtracting the mass of the filter. This method, however, has a limited accuracy, particularly for low emission vehicles. Both methods suffer a loss in accuracy when the source of the emitted particles produces lower emissions and thus require significantly longer testing for low emission combustors.

LII can fill the need for particulate measurements since the LII signal is proportional to a particulate volume fraction over a wide dynamic range. However, LII provides a relative measure of particulate concentrations and requires a calibration for quantification of particulate concentrations. Currently, calibration of the technique for absolute particulate concentrations may be made by in situ comparison of the LII signal to a system with a known particle volume fraction determined through traditional methods. Using this empirical calibration procedure LII has been used to measure particle volume fraction in steady-state and time-varying diffusion flames, premixed flames and within engines and in engine exhaust streams.

It is an object of the present invention to perform absolute light intensity measurements in LII and thus avoid the need for a calibration in a source of particulates with a known concentration. It is a further object of the invention to determine a particle volume fraction using absolute light intensity measurements in LII. This requires a knowledge of the particle temperature either from a numerical model of particulate heating or experimental observation of the particulate temperature.

It is an object of the invention to provide a method and an apparatus which are calibration independent for measuring particulate concentrations, i.e. they do not require a source of particulate of known concentration and particle type.

Further, the development of absolute light intensity measurements prepares the basis for providing portable LII instruments. This is particularly useful for applications of exhaust particulate measurements in engine test cells in laboratories, emissions compliance measurements and roadside checks, for applications of stack particulate measurements in furnaces and boilers, for airborne particulate monitoring, and for on-line process monitoring, where calibration in a source of particulates with a known concentration may be impractical.

SUMMARY OF THE INVENTION

The invention provides a method and an apparatus for the determination of particle volume fractions with laser induced incandescence (LII) using absolute light intensity measurements. This requires a knowledge of the particle temperature either from a numerical model of particulate heating or experimental observation of the particulate temperature. Further, by using a known particle temperature a particle volume fraction is calculated. This avoids the need for a calibration in a source of particulates with a known particle volume fraction or particle concentration. The sensitivity of the detection system is calibrated from an extended source of known radiance and then this sensitivity is used to interpret measured LII signals. This results in a calibration independent method and apparatus for measuring particle volume fractions or particle concentrations. A modeling process involves a solution of the differential equations describing the heat/energy transfer of the particle and surrounding gas, including parameters to describe vaporization, heat transfer to the medium, particle heating etc. The solution gives temperature and diameter values for the particles over time. These values are then converted to radiation values using Planck's equation. Thus, the method and the apparatus in accordance with the present invention do not require a source of known particulate concentration for calibration purposes.

In accordance with the present invention there is provided a method for determining a particle volume fraction from a laser induced incandescence signal comprising the steps of: calibrating a photodetector response; irradiating a volume of gas with a pulsed laser light beam, the volume of gas containing one or more particles, said pulsed laser light beam for causing an incandescence of said one or more particles; measuring a signal of incandescence intensity with a photodetector, said incandescence signal being one of a prompt signal within a period of substantially unchanged intensity after a laser light pulse, a time integrated signal over a duration of time after the laser light pulse, and a time dependent signal; calculating a particle radiation; and calculating the particle volume fraction from the signal of incandescence intensity and an absolute intensity.

In accordance with the present invention there is further provided a calibration independent method for determining a particle volume fraction from an LII signal comprising the steps of: (a) providing an extended source of known radiance with a known brightness temperature for calibrating a photodetection system prior to obtaining the LII signal, the extended source of known radiance being disposed in a LII signal generation region; (b) measuring a light intensity signal from the extended source of known radiance with the detection system, said light intensity signal being a count of photons; (c) calculating a source temperature from the light intensity signal measured in step (b) and the known brightness temperature of the extended source of known radiance; (d) calculating a source radiance from an emissivity of the extended source of known radiance as a function of temperature and wavelength; said source radiance being calculated at a predetermined wavelength; (e) determining a calibration factor for calibrating the photodetection system from the light intensity signal measured in step (b) and the source radiance of step (d); and (f) determining the particle volume fraction from an observed LII signal using the calibration factor.

In accordance with the present invention there is provided an apparatus for determining a particle volume fraction from a laser induced incandescence signal comprising: a laser for generating a pulsed laser light beam into a measurement volume, said pulsed laser light beam for causing a laser induced incandescence signal of one or more particles in the measurement volume; a calibrated photodetector for detecting the laser induced incandescence signal of the one or more particles; and a processor for calculating a particle volume fraction using the laser induced incandescence signal and a mathematical model including a particle property, a gas property, and a laser and laser light beam geometry property.

Advantageously, the method and the apparatus in accordance with the present invention avoid the need for calibration in LII measurements using a source of a known particle volume fraction. This creates the basis for providing a portable apparatus which is used with ease in a plurality of locations.

Additional advantages will be understood to persons of skill in the art from the detailed description of preferred embodiments, by way of example only, with reference to the following figures:

BRIEF DESCRIPTION OF THE DRAWINGS

Exemplary embodiments of the invention will now be described in accordance with the drawings in which.

Like numerals are used to indicate like elements.

DETAILED DESCRIPTION OF THE INVENTION

Laser Induced Incandescence (LII) is used as an optical diagnostic to measure particle volume fraction and particle size in gases and combustion flames even if they are turbulent flames. The method and the apparatus in accordance with the invention are optimized for soot particles but they work also with other refractory particles capable of absorbing laser light energy with an evaporation temperature sufficiently high to produce measurable incandescence, such as alumina, silica, titania, and many metals and metal oxides. LII occurs when a laser light beam encounters such particulate matter within a gas. The particulates absorb the laser light energy and heat up to incandescence temperatures, in the case of soot this is 4000° K. to 4500° K. The subsequent radiation is detected and recorded and is used to determine a relative particulate volume fraction. Further, by employing the long-term time constant or from absolute light intensity measurements the particle size is determined since the long-time cooling is dependent upon the diameter of the particle. A maximum particle temperature is controlled by the point at which particle evaporation becomes the predominant heat loss mechanism. A further increase in laser light energy then tends to result in an increase in the evaporation of the particles rather than an increase in the particle temperature. A resultant radiation, which is of a short duration and blue wavelength shifted relative to a particle radiation at normal gas temperatures, is readily detected. LII typically has a temporal resolution of 10 ns and is used to perform point measurements in gases.

Figure 1:
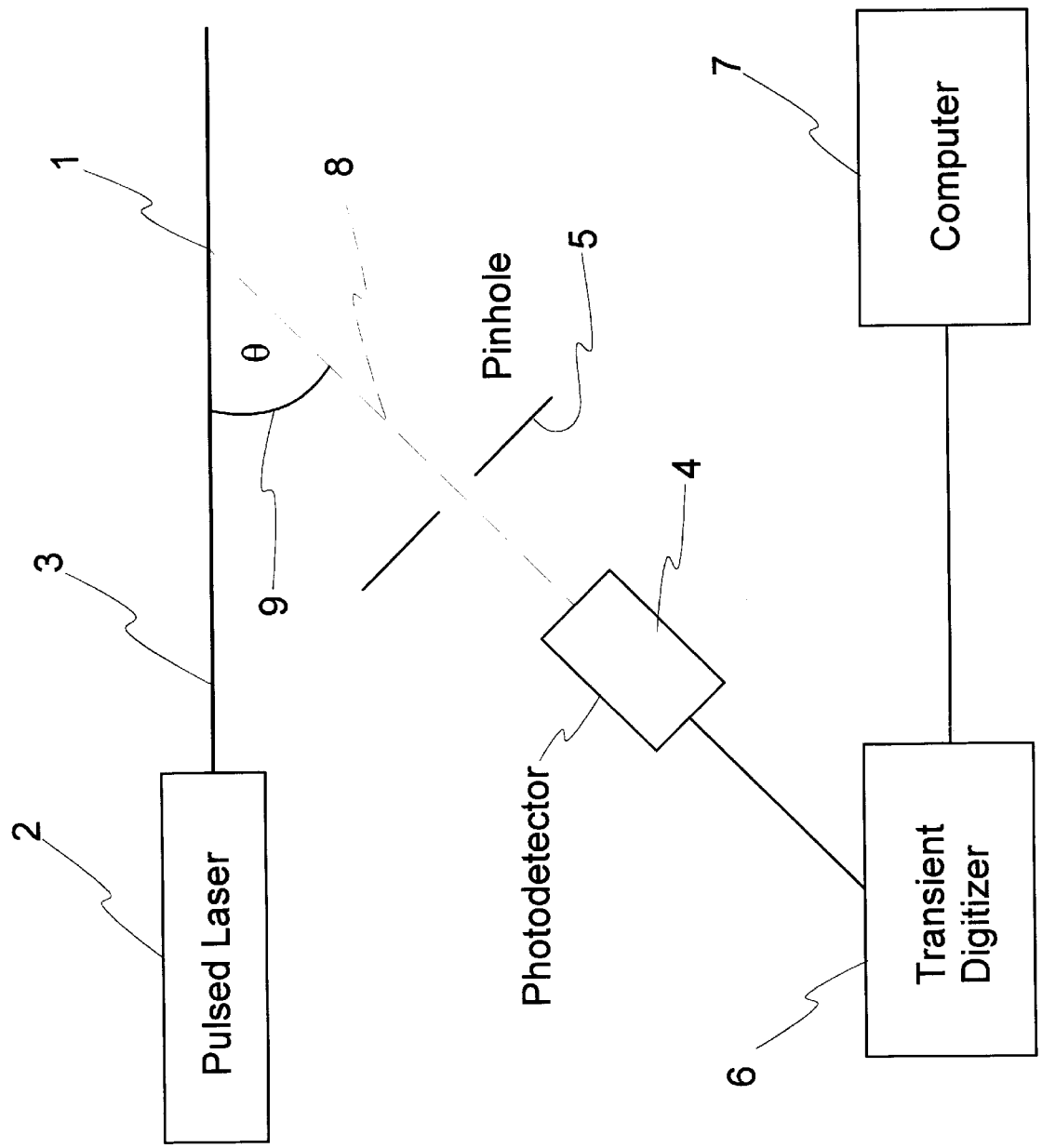
FIG. 1 shows a basic embodiment of the apparatus in accordance with the invention.

FIG. 1 shows a basic embodiment of the apparatus in accordance with the invention. A pulsed laser 2, capable of providing a laser light beam 3 with an energy density sufficient to reach evaporation temperature, e.g. 0.2 J/cm$^2$ for soot or greater, is passed through the medium in which a measurement is desired. Other possible energy sources in accordance with the invention are: a compact YAG laser, a drode laser, a high repetition rate laser, or other pulsed lasers. A photodetector 4, located at any arbitrary angle ($\theta$) 9 to the laser beam 3, detects the radiation produced by the interaction between the laser light beam and particles contained in the medium. Alternatively, other detectors, such as conventional or compact photomultipliers, a CCD camera, intensified CCD, Avalanche Photodiode detectors (APD), or Gallium-Arsenide (GaAs) detectors are used without departing from the scope of the invention. The measurement volume is defined by the field of view of the photodetector and the path of the laser light beam. In accordance with the invention, the measurement volume is chosen from a plurality of measurements, such as a point measurement, a line-of-sight measurement which measures the path along which the laser light beam travels, a full-plane measurement which samples the entire plane and not only a small part of the laser light sheet, a volume measurement which uses a giant laser light beam illuminating all particles at once, or an imaging measurement which measures the spatial distribution in a single laser light pulse using a CCD camera. The measurement volume I is optionally further defined by use of focussing lenses (not shown) for the laser beam 3, collection lenses for the photodetector(s) 4, or the use of an aperture 5 in the collection arm 8. The signal from the photodetector(s) 4 is recorded by a transient digitizer 6 for further processing, such as in a computer 7, or by a gated integrator (not shown).

Figure 2:
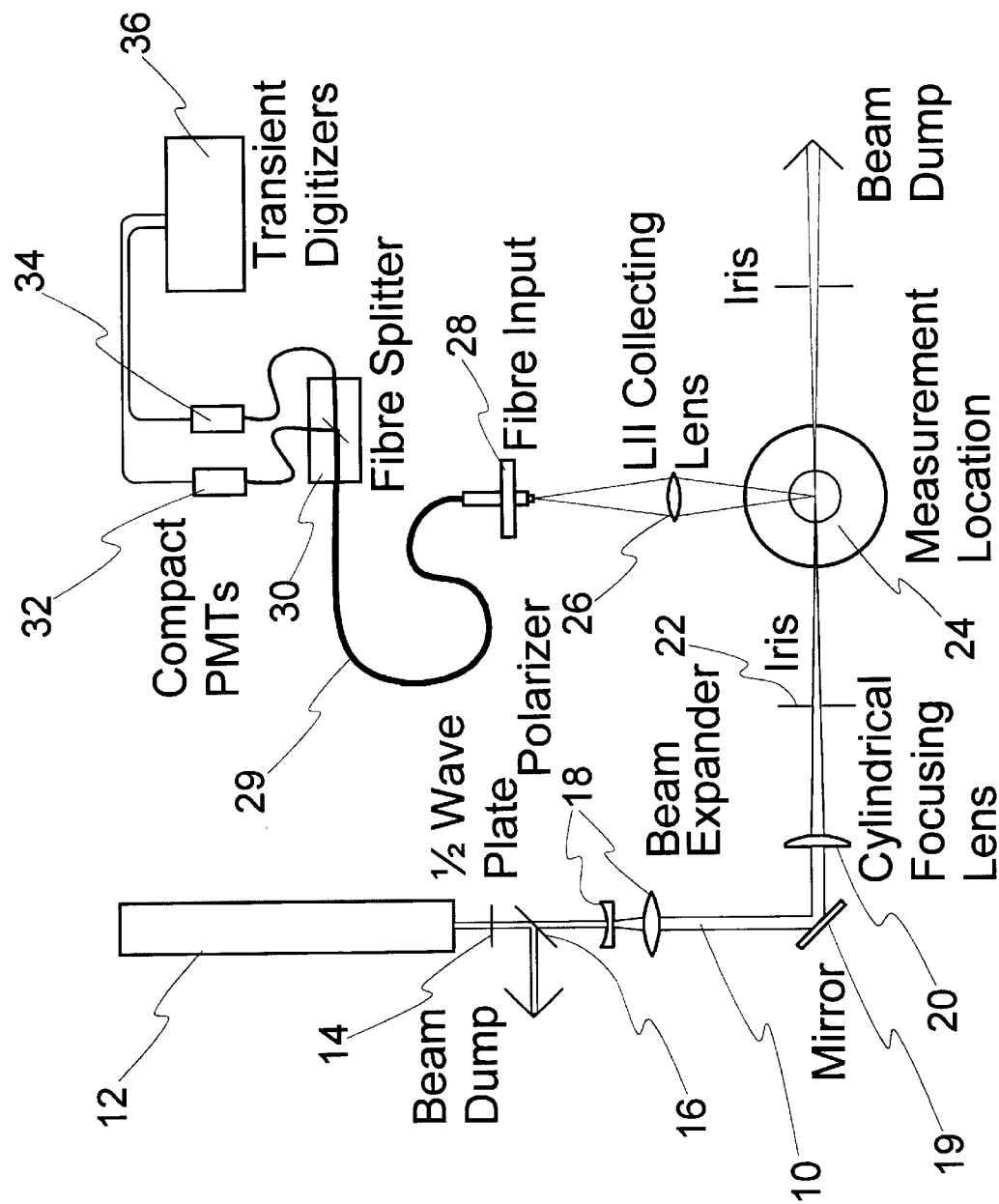
FIG. 2 is a schematic illustration of a more detailed embodiment of the apparatus in accordance with the present invention.

A more detailed embodiment of an apparatus in accordance with the present invention is illustrated in FIG. 2. A laser 12 directs a pulsed laser light beam 10 through a half wave plate 14 and polarizer 16 to a beam expander lens system 18. The laser light beam 10 is then passed to a mirror 19 from which it is reflected and passed through a focusing lens 20 for directing the laser light beam 10 down to an iris 22, through which the laser light beam 10 emerges as a laser light sheet through the measurement location 24. A collecting lens 26 directed toward the measurement location 24 perpendicular (for maximum spatial resolution) to the laser light beam collects and focuses the incandescent radiation generated by the laser light pulse into an optical fiber input 28. The measurement volume is determined by the width of the laser light sheet and the image of the fiber tip at the laser light sheet. The signal conducted by the fiber 29 is divided through a splitter 30 between a first detector 32, a photomultiplier connected to a gated integrator for detecting a prompt signal, and a second detector 34, a photomultiplier connected to a charge-coupled amplifier for collecting an integrated incandescence signal simultaneously with the prompt incandescence signal. Transient digitizers 36 are for converting the measured analog signal to a digital signal. Alternatively, the incandescence signal is sent to one detector and then digitized. The prompt and the integrated quantities are determined numerically from the digitized signal. In its simplest embodiment the apparatus can consist of a single detector which is connected to a gated integrator to measure the prompt incandescence signal or connected to a transient digitizer to measure the complete LII light pulse.

A preferred laser 12 is a Nd:YAG laser, such as a Continuum Surelite 1, because of its widespread availability, its ease of use, and its short duration Q-switched pulse. The Nd:YAG laser operates at its fundamental wavelength of 1064 nm,. The laser light beam quality is optimized by inserting an aperture of appropriate size in the laser cavity to produce a Gaussian profile in the near and far field. This modification reduces the maximum light energy available. Further attenuation of the laser light beam 10 may be controlled, by using a half wave plate 14 to rotate the plane of polarization in combination with a vertical polariser 16 to control the energy delivered to the measurement location. Other means such as a pocket cell or Kerr cell may be used to automatically attenuate the laser light beam to the desired laser light intensity. Of course other lasers can be used, such as a diode laser, a high repetition rate laser or other pulsed lasers, provided they deliver sufficient light energy to produce measurable incandescence given the light wavelength, beam geometry, and particulate composition in the excitation volume. A laser with a short light pulse duration, i.e. approximately smaller or equal to 20 ns, is preferred to minimize particle evaporation during the laser light pulse. For soot the light energy sufficient to raise the particulate temperature to evaporation is 0.2 to 0.8 J/cm$^2$.

The beam expander 18, focusing lens 20 and iris 22 optical system create a laser light sheet at the volume of the measurement location 24 having a Gaussian fit profile in substantially one plane only. The profile of beam light intensity is flat in two orthogonal planes. For maximum accuracy, the light beam intensity profile is measured. Creating a well defined known laser light intensity (laser light power per unit area, e.g. Watt/cm$^2$) with minimal variation over the measurement volume is important since the incandescent signal is highly dependent on the laser light energy intensity profile. In the model, energy values for particles other than at the peak light intensity is calculated using a uniform distribution of particles about the optic axis aligned with the Gaussian light intensity profile. The particles not located at the peak receive proportionally less light energy and produce a different incandescence signal, as determined in the calibration, which is added cumulatively to determine a total incandescence signal for a given time step. While in the preferred embodiment a Gaussian light intensity distribution of the fluence or light energy is used, a "top-hat" or square light intensity profile of the laser fluence having a constant light intensity throughout the laser light sheet would be beneficial. In principle any distribution of intensity can be used provided that its distribution through the measurement volume is measured. However, a more uniform light intensity profile ensures that the particulate temperatures are more uniform throughout the measurement volume. This increases the ease and accuracy of the numerical modeling and ensures that the average particulate temperature obtained from multi-wavelengths particulate measurements is more representative of the particle temperature in the measurement volume.

Conveniently the signal pick up is made with the optical fiber assembly creating a compact and versatile apparatus. The LII incandescence signal is focused by lens 26 on to an input fiber tip 28 matching the numeric aperture of the fiber. The LII signal is then conveyed to the light beam splitter 30 where the beam is collimated. An optical element then splits the collimated light beam into two or more parts, which are then focused into output fibers whose output terminates at the photodetector. The optical splitter either divides the input light beam into different wavelength bands or provides outputs of divided light intensity where all of the wavelengths are present. Optionally, interference filters 38 are inserted before the final focusing lens to further select the light wavelengths range going to each of the photodetectors.

The optical fiber provides for a better isolation of the light signal to the detectors, as well as providing a more compact assembly which is no longer dependent on free space optical alignment. The use of optical fibers also allows more flexibility in positioning the photodetectors and the single input fiber ensures that all photodetectors are viewing the same region of the gas. This may also be accomplished with a common aperture at the back focal plane of the receiver lens.

Figure 3:
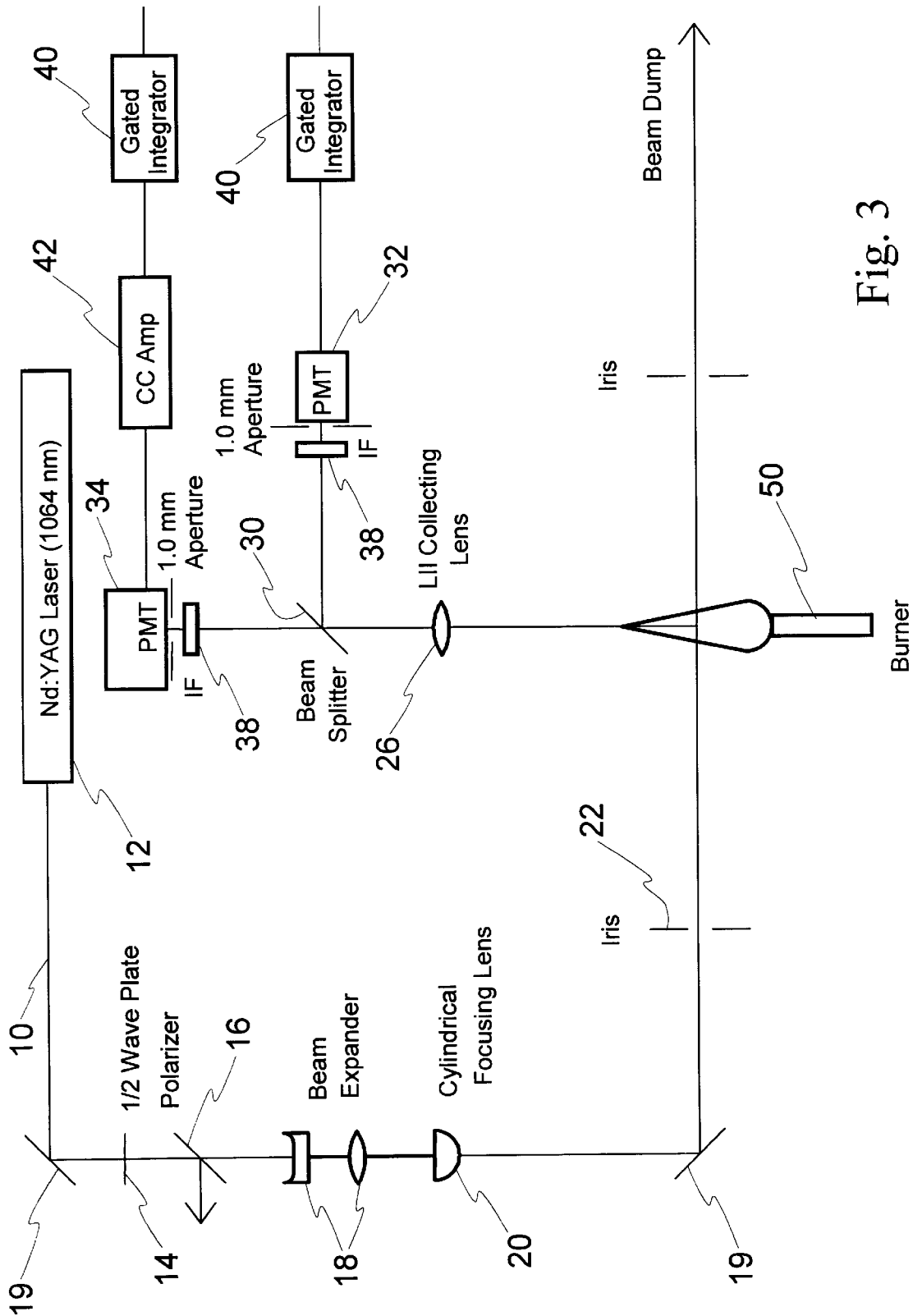
FIG. 3 is a schematic illustration of a further detailed embodiment of the apparatus in accordance with the present invention.

FIG. 3 is a schematic illustration of another embodiment of the apparatus in accordance with the present invention which uses conventional optics. As seen in FIG. 3, after being divided by the beam splitter 30, the light signals are passed through light interference filters 38 to select narrow nearly monochromatic wavelength regions for temperature detection.

FIG. 3 illustrates a bench scale model using a burner 50 having known controlled flame characteristics. The incandescence signals are detected by photomultipliers 32, 34, each controlled by a gated integrator 40 having a set gate width to measure a selected interval. The first detector 32 for detecting the prompt incandescence signal is connected directly to the gated integrator 40 whose gate width is set at 25 ns. The photodetectors 32, 34 could be compact photomultipliers, CCD cameras, or other photodetectors such as avalanche photodiodes (APD) or gallium arsenide (GaAs) detectors. The first photodetector 32 for detecting the prompt incandescence signal is connected directly to the gated integrator 40 with a gate width set at 25 ns. The photomultiplier 34 for detecting an integrated signal is connected to a charge-coupled amplifier 42 which measures the total charge collected during the LII signal period, i.e. approximately 1000 ns. Alternatively, a single photodetector could be used which would record the LII incandescence signal as a function of time thereby enabling the prompt and integrated signals to be extracted from the recorded signal. The gated integrator 40, connected to the charge coupled amplifier can readily be replaced by a single sample and hold circuit to measure the time integrated laser light pulse.

Collection of the incandescent light is done at two or more separate wavelengths using interference filters 38. A narrow wavelength region, typically 20 to 40 nm, is selected by the filters to obtain essentially two monochromatic signals. A first wavelength is selected which shows a change in light intensity due to the elevated temperature. At such high temperatures, the greatest shift in wavelength is noticeable in wavelengths close to the UV range. Light intensity detected at a second wavelength is measured such that the relative changes in the incandescence intensity/time profiles provide a measure of temperature/time. The ratio of the signal at two light wavelengths is related to the particle temperature.

This apparatus has proved effective, but is not limited too, or measuring particles approximately 10–100 nm in size and concentrations over the range from 0.01 to 10 ppm. The method is readily extended to lower concentrations by increasing the measurement volume or by averaging the LII light signal produced by many laser light pulses to increase the signal to noise ratio in the measurement.

Figure 8:
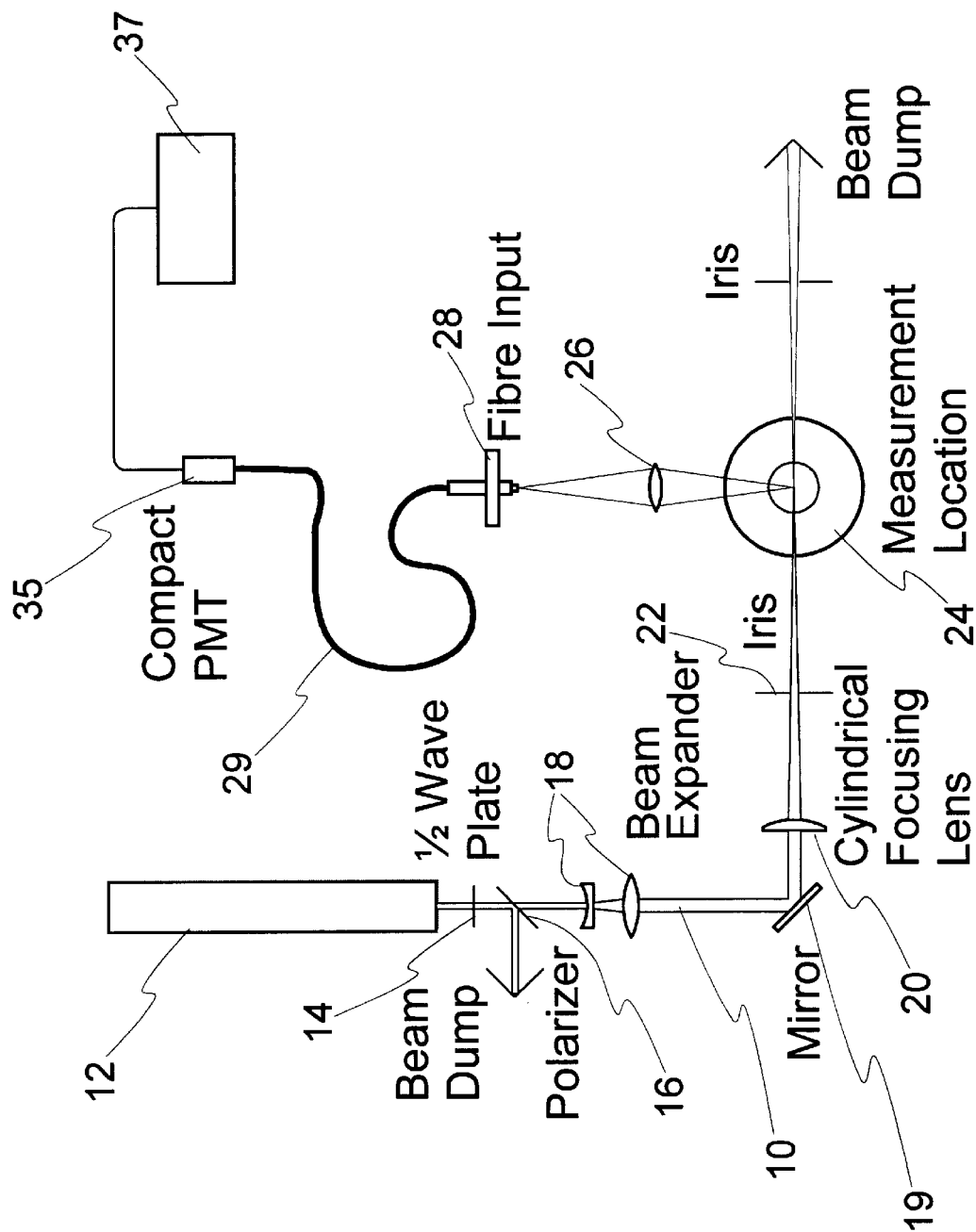
FIG. 8 is a schematic illustration of a further detailed embodiment having a single photodetector.

FIG. 8 shows an alternative embodiment of the present invention similar to the embodiment shown in FIG. 2, having a single photodetector 35, which is connected to a gated integrator 37 to measure the prompt incandescence signal. A single narrow wavelength band is collected. The particle temperature is then determined from the mathematical model. Alternatively, the single photodetector 35 is connected to a transient digitizer 37 to measure the complete incandescence signal. Advantageously, this economical system with an absolute light intensity calibration provides particle volume fraction measurements in a compact and practical arrangement.

Figure 4:
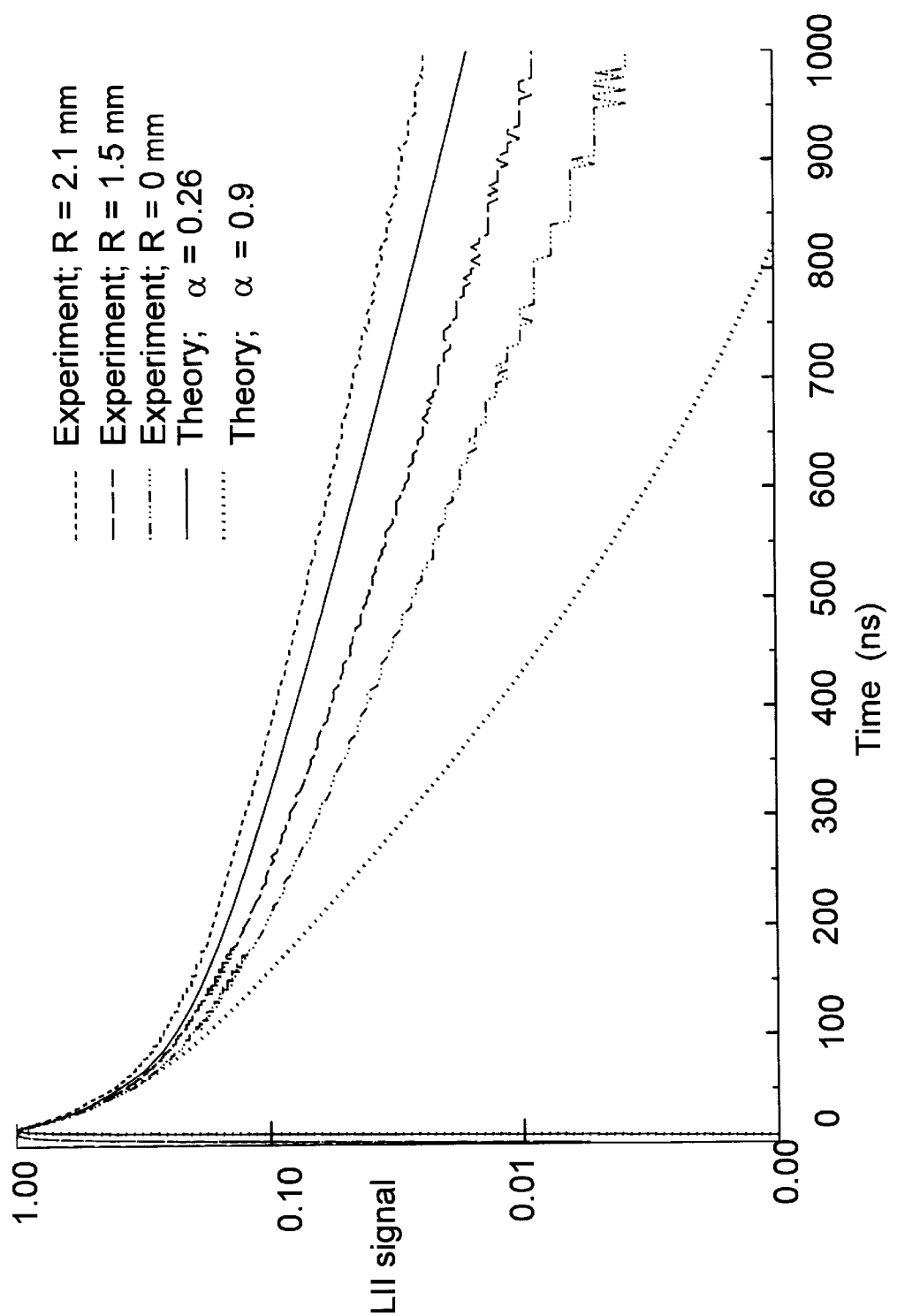
FIG. 4 shows a graph of a typical LII signal decay curve indicating variation in time constant in post evaporation (>300 ns) region showing measured and predicted values for a height of 40 mm in an ethylene/air flame.

The method in accordance with the invention directs a pulsed focused light beam from the laser 12 to provide a substantially instant light energy source ( approximately 10 ns duration) to a volume containing the particles 24. Several mJ of energy are sufficient to rapidly heat the particles to their evaporation temperature which is approximately 4500° K. in the case of soot. At this temperature radiate incandescence as they cool back to ambient temperature, the ambient temperature typically being 1500°–2000° K. in flames and less in other combustion systems, such as diesel engine exhausts. The incandescence signal is collected and imaged to a pair of detectors 32, 34. The first detector 32 provides a prompt measurement, at approximately 25 ns duration substantially at or near the peak intensity. The second detector 34 simultaneously collects an integrated signal through a charge-coupled amplifier 42 and a time gated integrator 40. The prompt and integrated signal provide a measurement of peak light intensity and total light intensity over time as the particles cool and the heat transfers to the surrounding gas. FIG. 4 is a graph of intensity over time illustrating decay curves of two incandescence signals. The ratio of the prompt and integrated signals is a function of the primary particle size. In addition, the incandescence from the prompt incandescence signal is proportional to the particulate volume fraction over a wide dynamic range.

The prompt incandescence signal is a substantially instantaneous measurement of short enough duration to see little change in the signal. The signal width is controlled through a time gated integrator 40. The integrated signal has a duration preferably beginning at the peak intensity and extending at least to a time at which the intensity is less than 10% of the peak intensity, so that a significant portion of the signal has been collected. A typical gate width of the integrated signal is 0.3 to 1.0 ms. It is desirable, although not essential, that the pulse duration be sufficiently short that there is little cooling of the particle by heat transfer to the surrounding medium. A laser pulse with a short light pulse duration, smaller or equal to 20 ns, will also minimize the amount of particle evaporation since the particle will be held at maximum temperature for a shorter period of time. Better accuracy is achieved if the prompt incandescence signal is taken at or close to the peak incandescence, eg. within 10–25 ns of the pulse initiation. However, a later measurement after some cooling has occurred is possible. The integrated incandescence signal should overlap with the prompt incandescence signal. A gated integrator is used to measure the output of the charge coupled detector although a simple sample and hold circuit could also be used. The charge coupled amplifier effectively integrates all of the LII light signal occurring in the LII light pulse (typical duration 1 $\mu$s) and the output of this photodetector at the end of the laser light pulse needs to be recorded.

The modeling process involves a solution of a differential equation describing the heat/energy transfer of the particle and the surrounding medium. This means parameters such as to describe vaporization, heat transfer to the medium, and particle heating are used in the modeling process. The solution of these differential equations gives the temperature and diameter values of the particles over time. These values are converted to radiation values using Planck's equation or other suitable theories. The model requires the simulation of particle morphology. A particle is typically idealized as an agglomeration of just touching primary particles. The absorption of radiation by such agglomerates is determined by the number of primary particles within the agglomerate and their diameter if the primary particles are not packed together too densely. Scanning electron microscope photographs show that such particle agglomerates are present in unique patterns which have been described by fractals.

The particle volume fraction, $f_v$, is described by nearly spherical primary particles which are characterized by a diameter $d_p$, the average number of primary particles per agglomerate $n_p$, and the number density of agglomerates N in the measurement volume as given below:

$$f_V = \frac{\pi}{6} N n_p d_p^2$$

One implementation of the measurement technique in accordance with the invention is also dependent on the mathematical model which maps a temperature history of the particles, from their peak incandescence and examining the decay rates. The model in accordance with the present invention better describes the decay curve of cooling for particles than seen in the prior art, therefore providing more accurate particle size interpretation. The model assumes a uniform distribution of particles along the optic axis aligned with the Gaussian profile of the laser intensity, compensating for less light energy received by particles not at the peak of the Gaussian light intensity profile in the measurement volume. Additional characteristics of the present model have greatly improved the accuracy of measurements, such as: the use of temperature dependent gas and particle properties; modeling a true profile of the laser light intensity in space and time instead of an assumed distribution; the use of measured particle properties, instead of assumed values from the literature; and light wavelength dependent filter transmission data rather than broad band sample collection.

Figure 5:
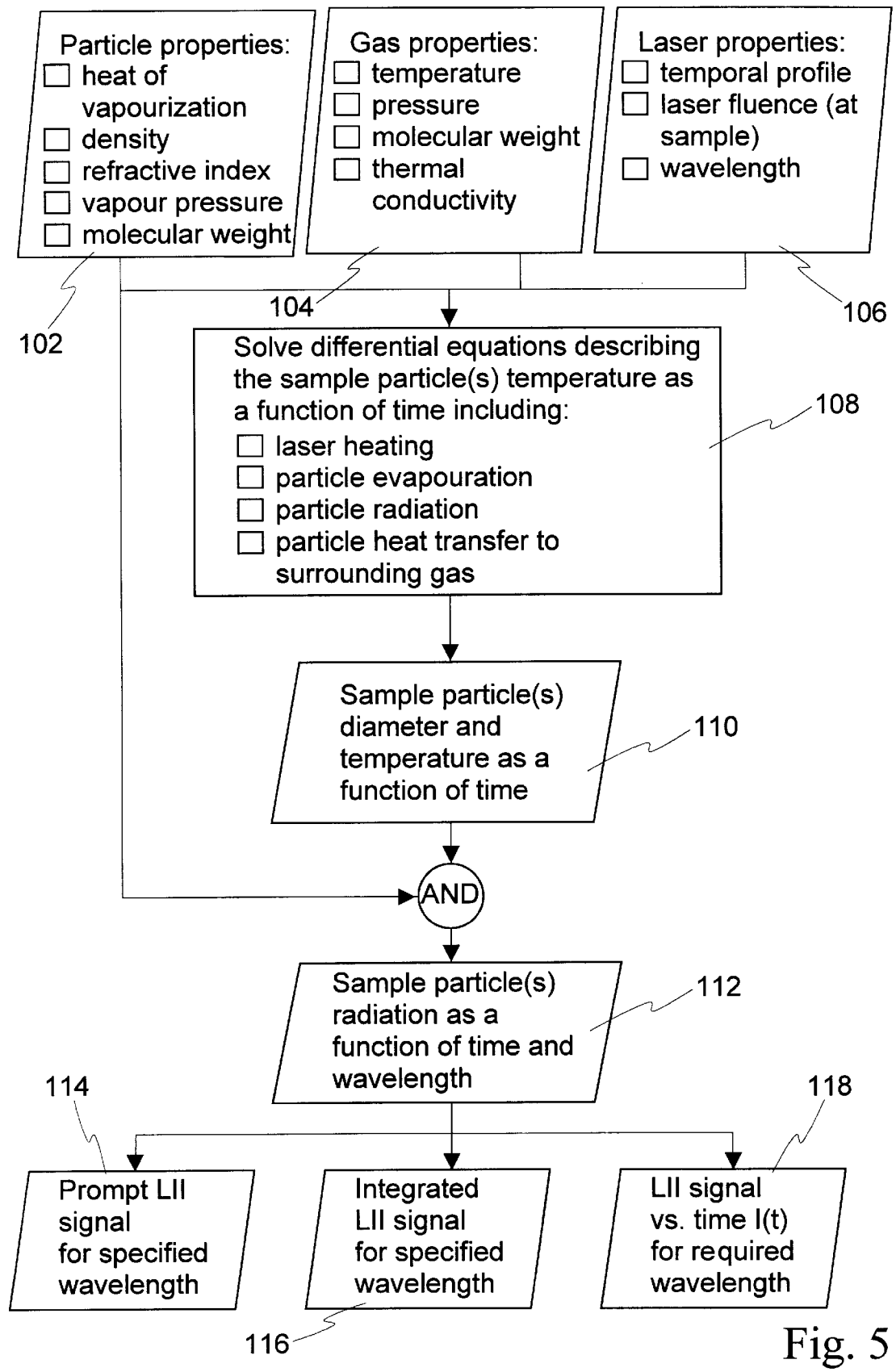
FIG. 5 shows a flow chart illustrating the mathematical modeling process.

Turning to FIG. 5, a flowchart of the modeling process used in accordance with an embodiment of the present invention is shown including the following parameters described below. The model is generally applicable to any particle which absorbs laser light energy with an evaporation temperature sufficiently high to produce measurable incandescence. The model considers particle agglomerates to be made up of uniform, non-overlapping primary spherical particles. The agglomerate volume is then found by multiplying the volume of a single primary particle by Np, the number of primary particles within the agglomerate. First the properties of the particle, the gas properties and the laser light properties are considered as outlined in blocks 102, 104 and 106 respectively. Particle properties 102 depend upon the type of particles and include heat of vaporization; density; refractive index; vapor pressure; and molecular weight. Gas properties 104 include temperature; pressure; molecular weight; and thermal conductivity. The laser light properties 106 include temporal profile; laser fluence spatial profile at the measurement volume; and wavelength. These properties are incorporated to solve the differential equations describing the sample particle temperature and diameter as a function of time outlined in block 108. These equations include laser light heating; particle evaporation; particle incandescence radiation; and particle heat transfer to the surrounding gas. These equations enable the determination of the sample particle diameter and temperature as a function of time indicated in block 110. Together with the particle properties 102, the sample particle diameter and the temperature as a function of time 110, the sample particle light radiation as a function of time and wavelength 112 are predicted for the prompt LII signal at an arbitrary specified wavelength 114, the integrated LII signal at an arbitrary specified wavelength 116, and a sample providing a decay curve of signal vs. time I(t) for an arbitrary wavelength 118. The measurements obtained from these three different ways are then used to determine the particle volume fraction and the particle size. The model used predicts signals for a laser light sheet with a fixed fluence across a thin edge and also for a laser sheet with a Gaussian light energy distribution which presents a real-life situation.

Alternatively, arbitrary light energy distributions are used provided that they are characterized and incorporated into the model.

The measurement of absolute light intensities in LII requires a knowledge of the particulate temperature determined from a numerical model of particulate heating or from an experimental measurement of the particulate temperature. An experimental measurement of the particulate temperature is better suited for the determination of particle volume fraction in the case of unknown particles. The particle volume fraction is determined either from a single particle emission calculated from the model or from a single particle emission calculated from an experimentally measured particle temperature in conjunction with an experimental measure of the total radiation.

The method is readily extended to any measured fluence distribution.

Figure 6:
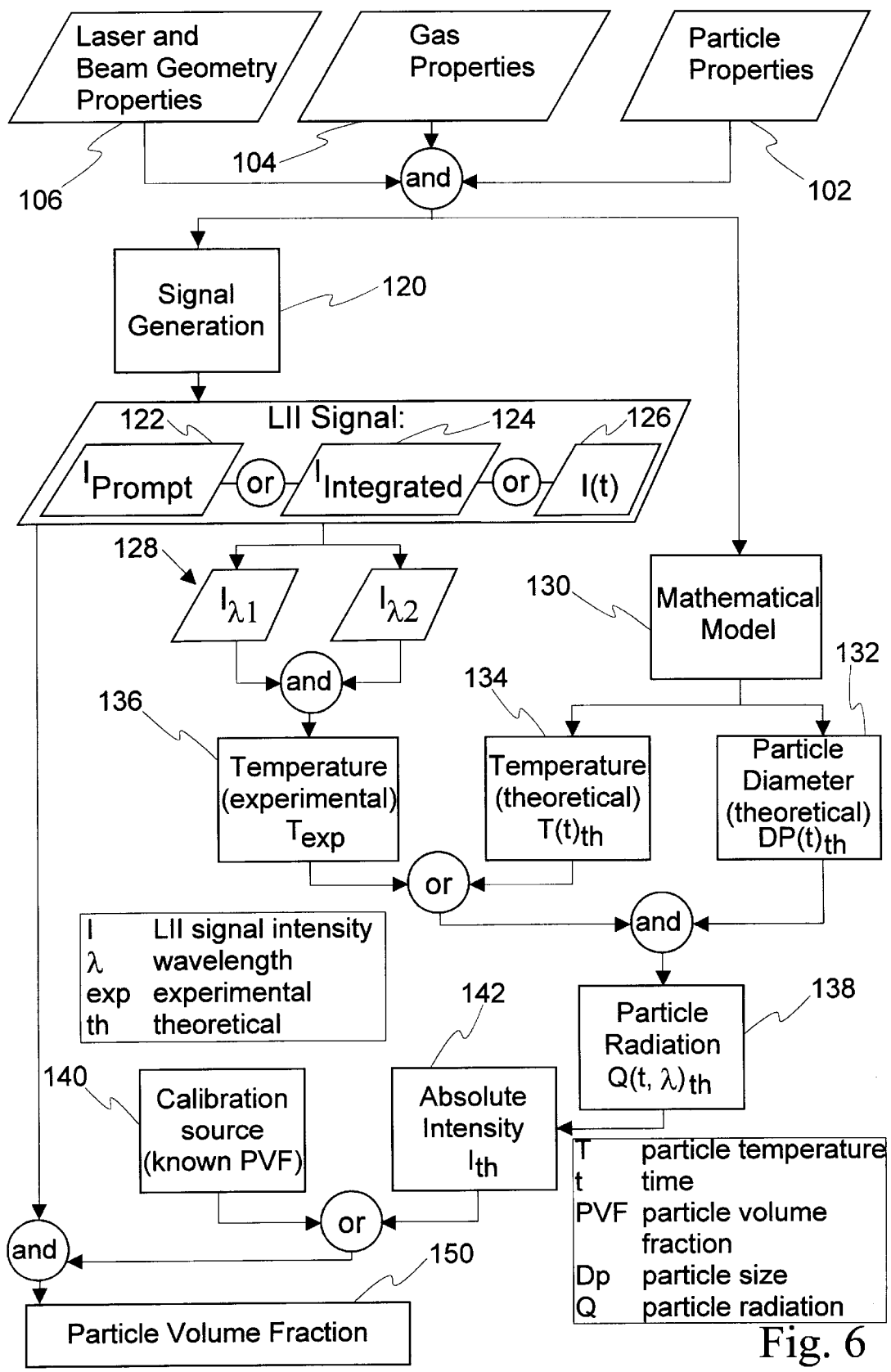
FIG. 6 shows a flow chart illustrating the method of determining particle volume fraction with LII.

FIG. 6 shows a flow chart illustrating the method of determining particle volume fraction with LII. The basic properties of the laser light and beam geometry 106, the gas 104 and the particle 102 contribute to the signal generation 120 and the mathematical model 130.

The particles do not have to be spherical provided that the model is modified to calculate the radiation from non-spherical particles. The signal generation 120 includes a prompt signal 122 and an integrated signal 124. Alternatively, a third signal 126 measures the signal decay over time at a large number of time points. Any of the prompt, integrated or time dependent signal measurements 122, 124, and 126 is sufficient in combination with a calibration source 140 or in combination with absolute light intensities 142 to determine the particle volume fraction 150. The prompt signal 122 is preferred since it is much less dependent on assumed particle size. The mathematical model 130 combines a theoretical particle diameter 132 based on the input properties 102, 104, 106 with a theoretical temperature 134 also based on the input properties, or with an experimental temperature 136. Experimental temperature 136 is determined by sampling the signal 126 with two or more different light wavelengths 128 which provide incandescence intensity signatures indicative of temperature on the light intensity decay curve. Temperature information 134 or 136 is combined with particle diameter to predict a net particle incandescence radiation to the surrounding gas 138. This value is used to provide an absolute light intensity 142 calibration of the system to avoid a conventional calibration. It is demonstrated in FIG. 6 that for absolute light intensity measurements the particle temperature is needed which is obtained either from the model or from LII signal measurements at at least two different wavelengths. For particles of known emissivity the particle temperature is proportional to the ratio of the LII signal intensity of the two measurements at different wavelengths. If the model is used to predict the particle temperature then a knowledge of the type of particle and its properties is needed as described in the flow chart of FIG. 5. Alternatively, traditional methods may be used to calibrate with a source of known particle volume fraction 140. This calibrated light radiation is used to determine a volume fraction measurement 150 of the prompt, integrated or time dependent signal 122, 124, 126.

It is shown in FIG. 6 that a particle radiation is used with an absolute light intensity measurement to determine the particle volume fraction. Generally in LII it is necessary to obtain a calibration before measuring volume fractions or particle concentrations. This is done by measuring the LII signal in a known cloud of a particle fraction. Absolute light intensity measurements in LII are advantageous since they alleviate measurements of particle volume fraction and particle sizes by avoiding prior calibration methods in referencing the measured LII signal to a known concentration. Thus with absolute light intensity measurements the measurement obtained for a particle volume fraction is based on the absolute light intensity measurement and a knowledge of the particle temperature. In accordance with an embodiment of the present invention a calibrated extended source of known light radiance is employed, such as a filament lamp, which generates a known light power at the LII photodetector. The LII detector signal produced by this incident intensity is recorded. This provides a calibration of the LII photodetector that can be used to determine the light intensity resulting from the LII particulate signals. Therefore, with absolute light intensity measurements in LII the signal from the lamp is used directly for the determination of particle volume fractions. Now, any time a signal is obtained with the photodetector, the light intensity that produced that signal is known. In order to determine the light intensity it is important to have a good model and to know the pattern of the laser light excitation. Preferably, all sample particles within a measurement volume are illuminated uniformly. This is a difficult task in real-life situations. It is related to a property of light that it is difficult to obtain a uniform profile when it is focused and a Gaussian light intensity profile is described here. The situation is particularly difficult when the light intensity varies in all spatial directions. Thus by using a small part of a sheet of laser light a uniform intensity variation is obtained in two directions and in the third direction, along the axis of viewing, a Gaussian light intensity distribution is obtained. It is important to know for absolute light intensity measurements how the particle is excited and to define the distribution of the radiation in space. The model employed has to correctly account for the- temperature of the number of particles within the measurement volume. For example, low energy excited particles are accounted for also with the model employed in accordance with the present invention and further discussed in detail below.

Thus, the particle concentration is determined by measuring the absolute LII signal, and compare that to the calculated theoretical light radiation per particle to calculate the concentration of particles. An extended source of known radiance (power/unit area of source-steradians-wavelength interval) whose brightness temperature is known is used to calibrate the detection system. In a preferred embodiment a strip filament is used as the extended source of known radiance. Errors associated with uncertainties in the filter characteristics, lens collection efficiency, aperture size, and optical system magnification are largely eliminated using this calibration procedure.

Alternatively to calculating the theoretical signal per particle from a solution of the model, the particle surface temperature is measured by recording two or more LII wavelengths simultaneously and using the ratio of these signals to obtain an experimental temperature. The experimental particle temperature rather than that obtained from the model is then used to calculate the radiation per particle. From the measured absolute LII signal light intensity and the calculated particle radiation intensity the number of particles is then calculated. As a result, the use of absolute light intensity measurements make particle volume fraction determinations more practical.

Figure 7:
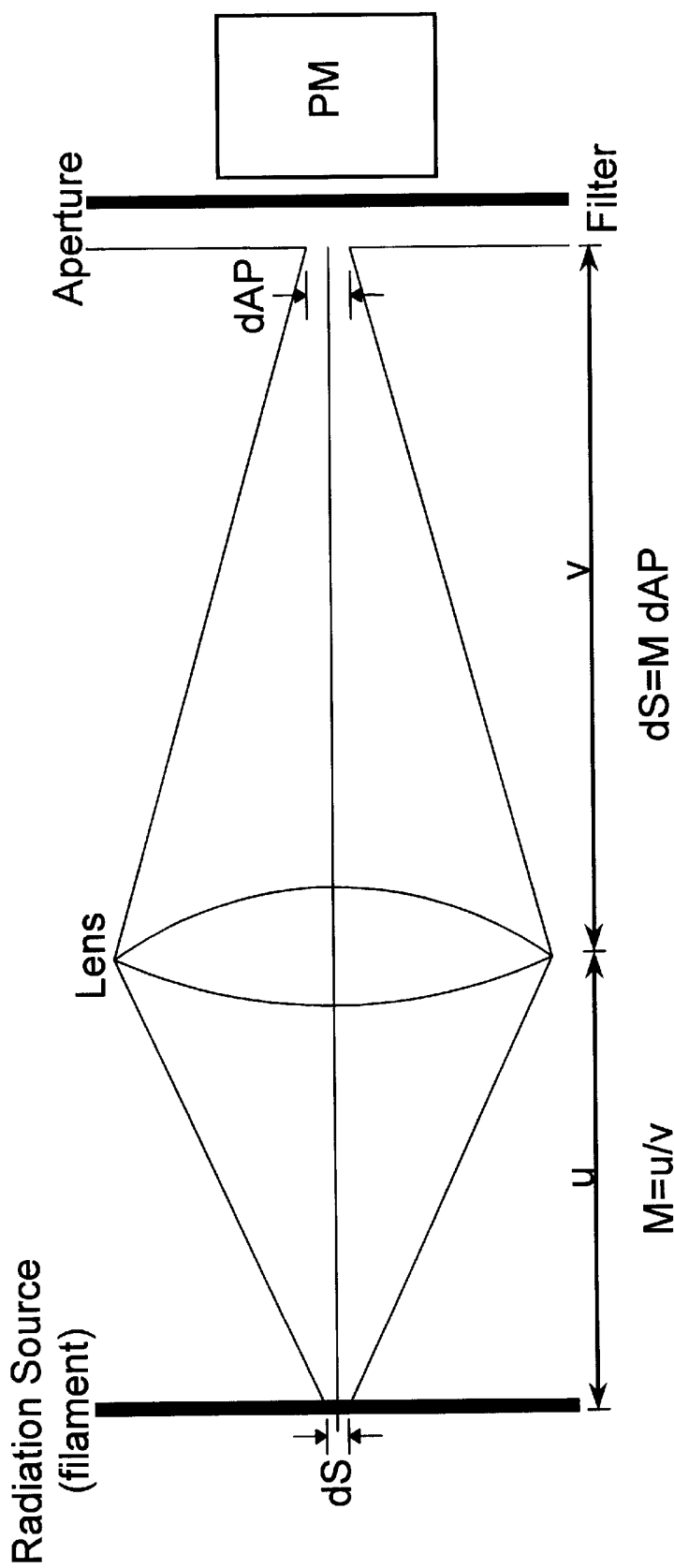
FIG. 7 shows an optical schematic for the absolute intensity calibration.

The optical schematic for the absolute light intensity calibration of the extended source of known radiance signal is shown in FIG. 7. In an embodiment of the invention an aperture having a diameter of 1.04 mm is placed in front of a filter and a photomultiplier (PM). This aperture is imaged with a lens onto a radiation source. In an embodiment of the invention the radiation source is a strip filament lamp and the aperture is imaged onto the filament of a calibrated strip filament lamp but other extended sources of known spectral radiance, e.g. a blackbody calibration source, can be used for this purpose. Furthermore, in an embodiment of the invention the lens has a focal length of 190 mm, a diameter of 54 mm, and a magnification of M=0.5. The magnification of the lens is determined from the distance u, i.e. the distance between the filament and the lens, and the distance v, i.e. the distance between the lens and the aperture, and equals M=u/v. The calibrated lamp is placed so that its filament is coincident with an LII signal generation region. The lamp, whose filament is 3×8 mm in an embodiment of the invention, has a known brightness temperature, at 654 nm, as a function of lamp current.

In another embodiment of the present invention the LII radiation is focussed on to an optical fiber tip. In this case the input aperture is the fiber core diameter.

The calibrated radiation source signal is determined by the spectral radiance of the lamp, i.e. the light power emitted per unit area, per unit solid angle, and per unit wavelength interval and is given by equation (1):

$$R_S(\lambda) = \frac{2c^2 h \varepsilon(\lambda, T)}{\lambda^5}\left[e^{\frac{hc}{k\lambda T}} - 1\right]^{-1} \quad (1)$$

$$= \frac{C_1 \varepsilon(\lambda, T)}{\lambda^5}\left[e^{\frac{C_2}{\lambda T}} - 1\right]^{-1}$$

wherein the first and second radiation constants are: $C_1 = 3.74177 \times 10^{-16}$ w m$^{-3}$ and $C_2 = 0.014388$ m K and $\epsilon(\lambda, T)$ is the emissivity as a function of wavelength and temperature.

The calibrated lamp has a known brightness temperature $T_B$ at a specific wavelength, such as at a wavelength of 654 nm. The brightness temperature $T_B$ is defined as the temperature at which a perfect black body would emit the same spectral radiance. The true filament temperature ($T_S$) is obtained from the brightness temperature $T_B$ as shown in equation (2) since the exponential term for the spectral radiance in equation (1) is >>1 for the temperatures and wavelengths considered in accordance with the present invention.

$$T_S = \left[\frac{1}{T_B} + \frac{\lambda_S}{C_2} \cdot \ln(\varepsilon(\lambda_S, T_S))\right] \quad (2)$$

The tungsten emissivity is required at the, initially unknown, filament temperature. As a first solution the emissivity at the brightness temperature TB is used to obtain an estimated filament temperature. The emissivity of tungsten at this estimated temperature is then used to obtain a new estimated filament temperature. Since the variation of tungsten emissivity with wavelength is not large, 2 or 3 iterations produce an estimate of $T_S$ that is correct within a fraction of a degree Kelvin.

Using a known emissivity of the filament, such as tungsten, as a function of temperature and wavelength the filament radiance is obtained at any desired wavelength from equation (1). The filament radiant power incident on the detector is given by equation (3):

$$P_{CAL} = M^2 A_{AP} \frac{A_L}{u^2} \int_\lambda R_S(\lambda) \tau(\lambda) d\lambda \tag{3}$$

where $A_{AP}$ is the area of the aperture, $\tau(\lambda)$ is the filter transmission as a function of light wavelength, and u and M are defined in FIG. 7 as the distance between the radiation source and the lens and as the lens magnification, respectively. An observed signal, $V_{CAL}$, from the calibration lamp then provides a detection system calibration in the following manner: $\eta = P_{CAL}/V_{CAL}$.

A theoretical LII intensity is determined as explained below. Using the calibration factor defined above the observed LII photomultiplier signal is converted to a detected intensity. This observed signal is then compared with the signal calculated by the LII model. The volume of the heated particle imaged onto the detector is defined by a cylinder with a cross-sectional area $M^2 A_{AP}$ and with a length equal to the thickness of the laser light sheet. Any variation in the imaged area over the narrow light sheet thickness is small and is usually ignored. The laser fluence is substantially constant across the end of the cylinder but has a Gaussian dependence along the cylinder axis, i.e. through the laser light sheet. If the dimension orthogonal to the light sheet is defined as x and the direction of the laser beam propagation is defined as z, then with the observed Gaussian behaviour of the laser light sheet, the fluence is described by equation (4):

$$F(x, y) = q_{TOT} \left[ \sqrt{\frac{1}{\pi}} \cdot \frac{1}{w_x} \exp\left(-\frac{x^2}{w_x^2}\right) \right] \left[ \sqrt{\frac{1}{\pi}} \cdot \frac{1}{w_y} \exp\left(-\frac{y^2}{w_y^2}\right) \right] \tag{4}$$

wherein $q_{TOT}$ is the laser light pulse energy and $w_x$ and $w_y$ are Gaussian 1/e half widths. In an embodiment of the invention the observed experimental $1/e^2$ half widths of 0.22 mm and 1.81 mm must be divided by $\sqrt{2}$. The peak fluence is then described by equation (5):

$$F(0) = q_{TOT} \frac{1}{\pi} \cdot \frac{1}{w_x} \cdot \frac{1}{w_y} \tag{5}$$

Since the radius of the cylindrical measurement volume region imaged (0.27 mm) is substantially smaller than $w_y$, the variation in the fluence in the y and z directions is ignored. The fluence in the imaged region is then given by equation (6):

$$F(x) = q_{TOT} \frac{1}{\pi} \cdot \frac{1}{w_x} \cdot \frac{1}{w_y} \exp\left(-\frac{x^2}{w_x^2}\right) \tag{6}$$

The total LII spectral power ($PS_p$) radiated into $4\pi$ steradians is calculated for a single particle. This total LII spectral power is the power per unit wavelength. $PS_p$ is a function of laser fluence, wavelength, and time and to a lesser extent a function of gas temperature and laser light pulse duration. The theoretical LII power ($P_p$) for a single particle corresponding to the experimental detection conditions is then described by equation (7):

$$P_p(F, t) = \frac{A_L}{4\pi u^2} \int_\lambda PS_p(F, \lambda, t) \tau(\lambda) d\lambda \tag{7}$$

The corresponding calculated energy over a 25 ns experimental detection gate is described by equation (8):

$$q_p(F) = \int_{t_0}^{t_0+25ns} P_p(F, t) dt \tag{8}$$

where $t_0$ is chosen to maximise the time integral to correspond to the experimental procedure of setting the gate position to maximise the LII signal. The wavelength integration is over the filter bandwidth, and $A_L/4\pi u^2$ is a fraction of the total radiation collected by the lens. For a total particle number density $n_p$ the theoretical total power ($PT_p$) is now calculated that would be observed from a single particle in the experiment by integrating PSP(F) over the region of space that is imaged onto the detector. This is described by equation (9):

$$PT_p = n_p M^2 A_{AP} \frac{A_L}{4\pi u^2} \int_\lambda \int_x PS_p(F(x), \lambda, t) \tau(\lambda) d\lambda dx \tag{9}$$

Whilst in this embodiment an example is given for Gaussian fluence profiles, in practice, any known distribution of fluence can be used and the integration over x (and y and z if necessary) in equation (9) can be performed over the required fluence F(x) (or F(x,y,z)).

In equation (9) the observed volume is defined as a cylinder of cross-sectional area $M^2 A_{AP}$ with a length equal to the sheet thickness. Here the spatial integral is performed across the laser light sheet using equation (6) to calculate the variation of the fluence with distance. Any variation of a particle concentration in the observation region is ignored.

The theoretical LII signal is compared to the experimental LII signal. The experimentally observed LII signal voltage, $V_{EXP}$ is converted to a power using the system calibration, $\eta$, as defined above, i.e., $P_{EXP} = \eta V_{EXP}$, and is then equated to the theoretical light intensity.

$$\frac{V_{EXP}}{V_{CAL}} M^2 A_{AP} \frac{A_L}{4\pi u^2} \int_\lambda R_S(\lambda) \tau(\lambda) d\lambda = \tag{10}$$

$$n_p M^2 A_{AP} \frac{A_L}{4\pi u^2} \int_\lambda \int_x PS_p(F(x), \lambda, t) \tau(\lambda) d\lambda dx$$

The total particle number density, $n_p$, is now calculated from equation (10) since the other quantities are measured or obtained from the theory. It is apparent from equation (10) that the magnification (M), the aperture size ($A_{AP}$), and the collection solid angle of the lens ($A_L/u^2$) are common to both sides of equation (10) and thus they cancel out. The calibration is independent of the exact value assumed for these quantities. The integration over the filter bandwidth is also common to both sides and largely cancels out. Thus, the radiation source, such as a strip filament calibration lamp, provides a source of known radiance, which is used for comparison with the particle radiation, independent of any exact knowledge of the filter characteristics, collection solid angle, or viewing region cross-sectional area. The filter transmission curve used in the integrations over the filter bandwidth in equation (10) does not strictly cancel since the calibration lamp radiance and the LII signals are also functions of wavelength. However, to a good approximation, the filter transmission curve is replaced by an equivalent filter with a centre wavelength $\lambda_c$, a bandpass $\Delta_f$, and a transmission $\tau_{max}$ where the latter is the observed peak transmission of the filter. The equivalent bandpass is given by equation (11):

$$\Delta_f = \frac{\int_\lambda \tau(\lambda) d\lambda}{\tau_{max}} \tag{11}$$

The integration is over the total filter bandwidth: The centre wavelength, $\lambda_c$, is the wavelength limit for which the integral in equation (11) is ½ the total integral over all incandescence wavelengths. The filter transmission is from $\lambda_c - \Delta_f/2$ to $\lambda_c + \Delta_f/2$. The integration in equation (10) is now replaced by up $\tau_p \Delta_f \cdot R(\lambda_c)$, where the lamp radiance is used at the centre of the filter bandwidth. The approximation to the total integral in equation (3) and the left hand side of equation (10) has an error of approximately 10% for a filter with a bandwidth of 40 nm, centred at 400 nm, and a filament temperature of 1600° K. This is the maximum error likely to be encountered in the calibration since the error decreases as the lamp filament temperature, or the particle temperature, or the centre wavelength increase. The error involved in similarly replacing the integration in equation (7) and the right hand side of equation (10) is smaller since the variation of the LII signal with wavelength is less than that of the calibration lamp. At typical laser heated particle temperatures the errors are <1%. For the lamp calibrations the final calibration for the error involved in replacing the integration with equation (11) is corrected using numerical estimates of the error.

The simplified calibration procedure for calculating the primary particle number density using the theoretically derived particle incandescence intensity is now described. The cancellation of the magnification, solid angle, and filter transmission in equation (10) leads to a considerable simplification of this equation. It also leads to an important increase in experimental accuracy in that small errors in the measurements of the magnification, solid angle and filter transmission largely cancel because they affect the calibration in the same way they affect the calculated theoretical intensity. Thus a simplified calibration is now performed where instead of equation (3) the filament radiance at the filter centre wavelength ($R_S(\lambda_c)$) is used. Equation (3) now becomes equation (3b):

$$P_{CAL} = M^2 A_{AP} \frac{A_L \tau_p \Delta_f}{u^2} R_S(\lambda_c) \tag{3b}$$

The calibration constant/factor $\eta$ is now calculated using $\eta = R_S(\eta_c) V_{CAL}$. The calibration factor $\eta$ is now in units $W \cdot cm^{-2} \cdot V^{-1}$ unit wavelength interval$^{-1}$ or $V^{-1} \cdot cm^{-3} \cdot sr^{-1} \cdot W$.

Equation (7) now becomes equation (7b):

$$P_p(F, t) = \frac{A_L \tau_p \Delta_f}{4\pi u^2} PS_p(F, \lambda_c, t) \tag{7b}$$

and thus equation (10) becomes equation (10b):

$$V_{EXP} \cdot \eta = \frac{V_{EXP}}{V_{CAL}} \cdot R_S(\lambda_c) = \frac{\eta_p}{4\pi} \int_x PS_p(F(x), \lambda_c, t) dx \tag{10b}$$

The particle number density, $n_p$ is now calculated from equation (10b). The particle volume fraction is then given by equation (11.5):

$$f_V = \pi d_p^3 \frac{n_p}{6} \tag{11}$$

Since $P_p$ and thus $PS_p$ are proportional to the primary particle volume, i.e. $d_p^3$, the particle volume fraction is independent of the exact value of $d_p$ assumed in equations (10b) and (11.5). Thus the product of $$\frac{\pi d_p^3 n_p}{6}$$

or the volume fraction is determined rather than the $d_p$ and $n_p$ separately. A determination of $d_p$ from the LII signal measurement would then be required to obtain $n_p$.

A simplified calibration procedure for calculating the particle volume fraction using experimentally derived particle temperatures is now described. If two or more signals at independent wavelengths are recorded an average particle surface temperature across the laser light sheet is calculated by using the ratio of the observed signals, corrected for detection sensitivity, and the known particle light absorption cross sections. The power radiated by a single particle of diameter $d_p$ is given by equation (12):

$$P_p(\lambda) = \frac{8\pi^3 c^2 h}{\lambda^6} \left[ e^{\frac{hc}{k\lambda T}} - 1 \right]^{-1} d_p^3 E(m) \tag{12}$$

where m, a complex refractive index, is a function of wavelength. The ratio of the powers at two wavelengths is then given by equation (13):

$$\frac{P_p(\lambda_1)}{P_p(\lambda_2)} = \frac{\lambda_2^6}{\lambda_1^6} \frac{\left[ e^{\frac{hc}{k\lambda_2 T}} - 1 \right]}{\left[ e^{\frac{hc}{k\lambda_1 T}} - 1 \right]} \frac{E(m_{\lambda_1})}{E(m_{\lambda_2})} \tag{13}$$

The observed signal ratio at the two wavelengths $V_{EXP}(\lambda_1)/V_{EXP}(\lambda_2)$ is converted to relative powers ($P_E$) using the calibration factors as described in equation (14):

$$\frac{P_{EXP}(\lambda_1)}{P_{EXP}(\lambda_2)} = \frac{V_{EXP}(\lambda_1)}{V_{EXP}(\lambda_2)} \frac{\eta(\lambda_1)}{\eta(\lambda_2)} \tag{14}$$

Using this experimentally determined power ratio and the known values of E(m), equation (14) is solved for T. In this case it is only the variation of the particle absorption cross-section with light wavelength that is important in determining the particle surface temperature. This temperature, derived from a power ratio measurement at two incandescence wavelengths, represents some average particle surface temperature through the Gaussian light sheet. The integral in the right hand side of equation (10b) is now approximated as described in equation (15):

$$P_p(T_{AV}, \lambda_c)\sqrt{\pi}w_x \quad (15)$$

where the experimental particle temperature is used rather than that derived from the model to calculate $P_p$ and thus equation (10b) becomes equation (10c):

$$V_{EXP} \cdot \eta = \frac{V_{EXP}}{V_{CAL}} R_F(\lambda_c) = \frac{n_p}{4\pi} P_p(T_{AV}, \lambda_c)\sqrt{\pi}\, w_x \quad (10b)$$

The primary particle number density, $n_p$, is now calculated from equation (10c) since all other quantities are known. Equation (10c) is an approximation since the average temperature does not strictly reproduce the absolute radiance. Direct numerical simulation of this averaging approximation compared to the correct radiant powers indicated that it underestimates the power by ~20%. The derived particle number density derived from the approximation in equation (10c) will then be ~20% high. In practice using the numerical simulation results to apply an appropriate correction can reduce this error. Numerical simulation also shows that a laser fluence profile that is closer to "top-hat" profile, i.e. a constant fluence across the laser light sheet, results in much smaller errors.

The following is a glossary of terms used in the above described absolute light intensity measurements:

Upper-case:

| | |
|---|---|
| A | area (m$^2$) |
| AP | aperture |
| C$_1$ | first radiation constant (3.7417749 · 10$^{-16}$ W · m$^2$) |
| C2 | second radiation constant (0.01438769 m · K) |
| E(m) | refractive index dependent function |
| F | fluence (J · cm$^{-2}$) |
| M | magnification |
| P | power (W) |
| PS | spectral power (W · nm$^{-1}$) |
| PT | total power (W) |
| R | spectral radiance (W · m$^{-2}$ · sr$^{-1}$ nm) |
| S | radiation source (filament) |
| T | temperature (K) |

Lower-case:

| | |
|---|---|
| c | speed of light (2.99792458 · 10$^8$ m · s$^{-1}$) |
| d | primary particle diameter (nm) |
| fv | volume fraction (ppm) |
| h | Planck's constant (6.6260755 · 10$^{-34}$ J · s) |
| k | Boltzmann's constant (1.380658 · 10$^{-23}$ J · K$^{-1}$) |
| m | refractive index |
| n | number density (m$^{-3}$) |
| q | energy (J) |
| t | time (ns) |
| u | object distance (m) |
| v | image distance (m) |
| w | width (m) |
| x, y, z | Cartesian coordinates (m) |

Greek symbols:

| | |
|---|---|
| $\Delta_f$ | filter bandwidth (nm) |
| $\epsilon$ | emissivity |
| $\lambda$ | wavelength of light (nm) |
| $\lambda_s$ | calibration wavelength of radiation source (nm) |
| $\tau$ | filter transmission |
| $\eta$ | calibration factor |

Subscripts:

| | |
|---|---|
| AP | aperture |
| AV | average |
| B | brightness |
| c | centre |
| CAL | calibration |
| EXP | experimental |
| f | filter |
| L | lens |
| max | maximum |
| p | particle |
| S | radiation source (filament) |
| TOT | total |
| V | volume |

The equation for the heat transfer energy balance is presented in equation (16):

$$C_a q - \frac{2k_a(T-T_0)\pi D^2}{(D+G\lambda_{MFP})} + \frac{\Delta H_v}{M_V}\frac{dM}{dt} + q_{rod} - \frac{1}{6}\pi D^3 \rho_S c_s \frac{dT}{dt} = 0 \quad (16)$$

Equation (16) includes a term for the absorbed laser light energy assuming the particles are agglomerates of just touching spheres made up of primary particles and that primary particles are in the Rayleigh limit. The equation further includes a term for the heat transfer to the surrounding gas, the evaporation of carbon, the net particle radiation to the surroundings, and finally the particle heating.

A glossary of terms for equation (17) follows below:

| | |
|---|---|
| C$_a$ | soot particle optical absorption cross section (m$^2$) |
| C$_s$ | specific heat of carbon |
| d$_p$ | primary soot particle diameter |
| G | geometry dependent heat transfer factor G = 8f/($\alpha(\gamma+1)$) |
| $\Delta$H$_v$ | heat of vaporisation of carbon |
| k$_a$ | thermal conductivity of ambient air |
| M$_v$ | molecular weight carbon vapour |
| M | mass of carbon |
| q | laser light intensity |
| T | soot surface temperature |
| T$_0$ | gas temperature |
| $\lambda_{MFP}$ | the mean free path $\lambda_{MFP}$ = 1/(2$^{0.5}\pi(\sigma_{AB})$2 in rigid sphere approximation (m) |
| $\rho$s | density of soot (kg/m$^3$) |

The above-described embodiments of the invention are intended to be examples of the present invention and numerous modifications, variations, and adaptations may be made to the particular embodiments of the invention without departing from the scope and spirit of the invention, which is defined in the claims.

What is claimed is:

1. A method for determining a particle volume fraction from a pulsed laser induced incandescence signal comprising the steps of:
   calibrating a photodetector response to light intensity;
   irradiating a volume of gas with a pulsed laser light beam, the volume of gas containing one or more particles, said pulsed laser light beam for causing an incandescence of said one or more particles;
   measuring a signal of incandescence intensity with a photodetector, said incandescence signal being one of a prompt signal within a period of substantially unchanged intensity after a laser light pulse, a time integrated signal over a duration of time after the laser light pulse, and a time dependent signal;
   calculating radiation of a particle independent of measured signal; and
   calculating the particle volume fraction from the signal of incandescence intensity and an absolute intensity.

2. A method as defined in claim 1 wherein the step of calibrating the photodetector response for providing an absolute intensity calibration comprises the steps of:

providing an extended source of known radiance with a known brightness temperature for calibrating the photodetector prior to irradiating the volume of gas with the pulsed laser light beam, the extended source of known radiance being disposed in an laser induced incandescence signal generation region;

measuring a light intensity signal from the extended source of known radiance with the photodetector, said light intensity signal being a count of photons;

calculating a temperature of the extended source of known radiance from the light intensity signal and the known brightness temperature of the extended source of known radiance;

calculating a radiance from an emissivity of the extended source of known radiance as a function of temperature and wavelength; said radiance being calculated at a predetermined wavelength; and determining a calibration factor for calibrating the detector response from the measured light intensity signal and the calculated filament radiance.

3. A method as defined in claim 2 wherein the extended source of known radiance is a strip filament lamp.

4. A method as defined in claim 2 wherein the particle radiation is calculated from a particle diameter and a particle temperature.

5. A method as defined in claim 4 wherein the particle diameter is obtained from a mathematical model including a particle property, a gas property, and a laser and laser light beam geometry property.

6. A method as defined in claim 5 wherein the particle temperature is obtained from one of a theoretical temperature and an experimental temperature, said theoretical temperature obtained from the mathematical model and said experimental temperature obtained from the signal of incandescence intensity measured at two different light wavelengths.

7. A method as defined in claim 6 wherein the experimental temperature is calculated from a ratio including the signal of incandescence intensities measured at the two different light wavelengths.

8. A method as defined in claim 7 wherein the time integrated signal is detected over a duration comprising a major portion of a total incandescence intensity.

9. A method as defined in claim 8 wherein the time integrated signal is detected over a duration from a time at substantially a peak incandescence intensity to a time at which the incandescence intensity is less than 10% of the peak incandescence intensity.

10. A method as defined in claim 8 wherein the prompt signal is detected substantially at a peak incandescence intensity.

11. A method as defined in claim 10 wherein the pulsed laser light beam is optimized to have a controlled spatial profile in a near field and a far field.

12. A method as defined in claim 11 wherein the pulsed laser light beam is focused to form a laser sheet through the signal generation region.

13. A calibration independent method for determining a particle volume fraction from an laser induced incandescence signal comprising the steps of:

(a) providing an extended source of known radiance with a known brightness temperature for calibrating a photodetection system prior to obtaining the laser induced incandescence signal, the extended source of known radiance being disposed in a laser induced incandescence signal generation region;

(b) measuring a light intensity signal from the extended source of known radiance with the detection system, said light intensity signal being a count of photons;

(c) calculating a source temperature from the light intensity signal measured in step (b) and the known brightness temperature of the extended source of known radiance;

(d) calculating a source radiance from an emissivity of the extended source of known radiance as a function of temperature and wavelength; said source radiance being calculated at a predetermined wavelength;

(e) determining a calibration factor for calibrating the photodetection system from the light intensity signal measured in step (b) and the source radiance of step (d); and (f) determining the particle volume fraction from an observed laser induced incandescence signal using the calibration factor.

14. A method as defined in claim 13 wherein the observed laser induced incandescence signal is one of a prompt signal within a period of substantially unchanged intensity after a laser beam light pulse, a time integrated signal over a duration of time after the laser beam light pulse, and a time dependent signal.

15. A method as defined in claim 14 further including the step of determining a particle diameter from a mathematical model for determining the particle volume fraction.

16. A method as defined in claim 15 wherein the mathematical model assumes a uniform distribution of one or more particles along an optic axis aligned with a Gaussian profile of a laser light intensity.

17. An apparatus for determining a particle volume fraction from a laser induced incandescence signal comprising:

a laser for generating a pulsed laser light beam into a measurement volume, said pulsed laser light beam for causing a laser induced incandescence signal of one or more particles in the measurement volume;

a calibrated photodetector for detecting the laser induced incandescence signal of the one or more particles; and a processor for calculating a particle volume fraction using the laser induced incandescence signal and a mathematical model including a particle property, a gas property, and a laser and laser light beam geometry property.

18. An apparatus as defined in claim 17 wherein the mathematical model for calculating a particle volume fraction includes a particle radiation, said particle radiation being calculated from a particle diameter and a particle temperature, said particle diameter being obtained from the mathematical model, said particle temperature being obtained from one of a theoretical particle temperature and an experimental particle temperature, said theoretical particle temperature being obtained from the mathematical model and said experimental particle temperature being obtained from the laser induced incandescence signal measured at two different wavelengths.

19. An apparatus as defined in claim 18 wherein said laser induced incandescence signal is selected from one of: a prompt signal within a period of substantially unchanged intensity after a laser pulse; a time integrated signal over a duration of time after the laser light beam pulse; and a time dependent signal.

20. An apparatus as defined in claim 18 further including an extended source of known radiance having a known brightness temperature for calibrating a detector response for providing an absolute intensity calibration of the calibrated detector prior to irradiating the measurement volume with the pulsed laser light beam, the extended source of known radiance being disposed in an laser induced incandescence signal generation region.

21. An apparatus as defined in claim 20 wherein the extended source of known radiance is a strip filament lamp.

22. An apparatus as defined in claim 20 including at least two filters associated with the calibrated detector for filtering the laser induced incandescence signals at at least two different wavelengths for obtaining the experimental particle temperature.

23. An apparatus as defined in claim 22 including collecting optics for directing the laser induced incandescence signal to the calibrated detector and wherein the measurement volume comprises an intersection of a collection diameter determined by the collecting optics and the pulsed laser light beam.

24. An apparatus as defined in claim 23 further including optical elements for optimizing the pulsed laser light beam to pass through the measurement volume having a controlled spatial intensity profile in a near field and a far field.

* * * * *